United States Patent
Niedermeyer

[19]
[11] Patent Number: 6,092,242
[45] Date of Patent: Jul. 25, 2000

[54] UNDERGARMENT ASSEMBLY

[76] Inventor: William P. Niedermeyer, 1024 Mt. Mary Dr., Green Bay, Wis. 54311

[21] Appl. No.: 09/240,900

[22] Filed: Jan. 29, 1999

Related U.S. Application Data

[63] Continuation-in-part of application No. 08/889,461, Jul. 8, 1997, Pat. No. 5,864,890.
[51] Int. Cl.[7] .................................................. A41B 11/00
[52] U.S. Cl. ...................... 2/400; 2/403; 2/406; 604/385.1
[58] Field of Search .................................. 2/79, 83, 78.2, 2/227, 111, 400–409, 69; 604/385.1, 385.2, 386–398

[56] References Cited

U.S. PATENT DOCUMENTS

| | | | |
|---|---|---|---|
| 620,317 | 2/1899 | Hatch | 2/78.1 |
| 1,973,963 | 9/1934 | Nishimoto | 2/408 |
| 2,476,585 | 7/1949 | Cohen | 2/408 |
| 3,890,973 | 6/1975 | Davis et al. | 604/385.1 |
| 5,014,364 | 5/1991 | Orr | 2/408 |
| 5,669,902 | 9/1997 | Sivilich | 604/396 |

*Primary Examiner*—Gloria Hale

[57] ABSTRACT

An unfolded hour-glass shaped undergarment brief assembly comprising two shaped half width segments superposed in overlapping relationship with about half of the overlapped central area between segment halves bonded to form a unitary rear panel. The other half of the overlap is left unbonded to provide an opening in the front panel. The outer margin of the opening can be reinforced by enclosure within a v-folded strip and the overlapped segments are held together by a releasable fastening means that joins the two front panel half width segments. Tapes or other fastening means protrude from the side margins and are used to complete the waist and leg apertures after the front half is folded upward around the user. Release strip covered adhesive receptor areas are provided to accept an absorbent pad insert. The central crotch section can have flap extensions that are folded around edges of the pad insert to hold it in place and prevent side leakage from the pad.

19 Claims, 2 Drawing Sheets

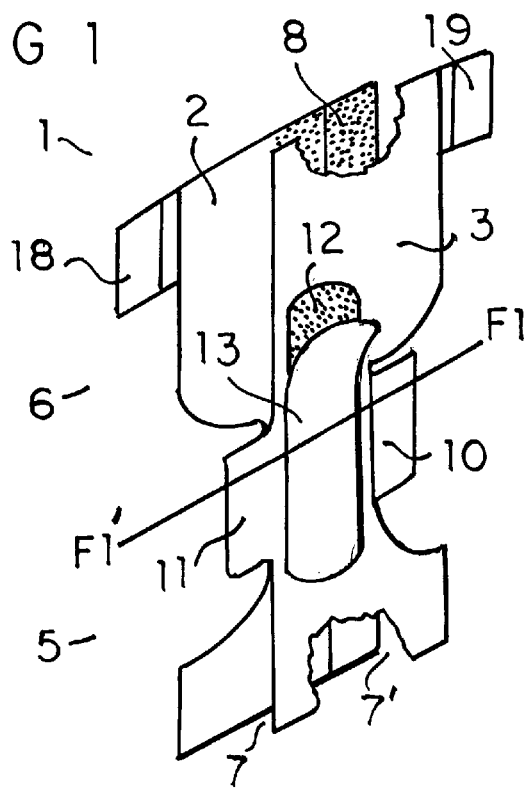
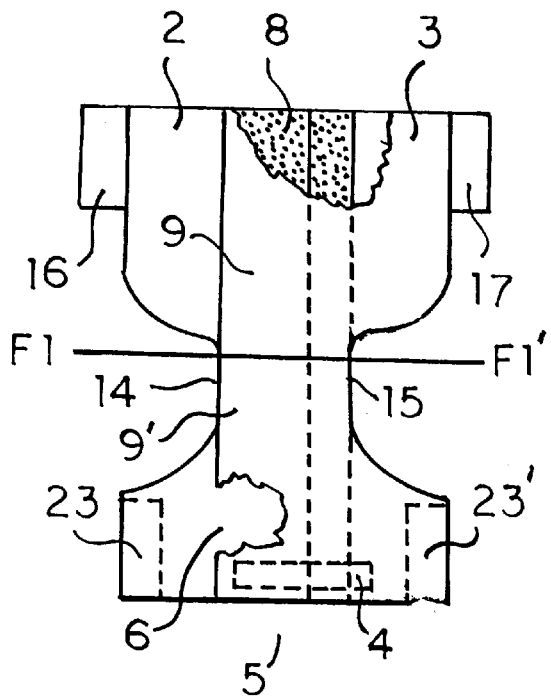
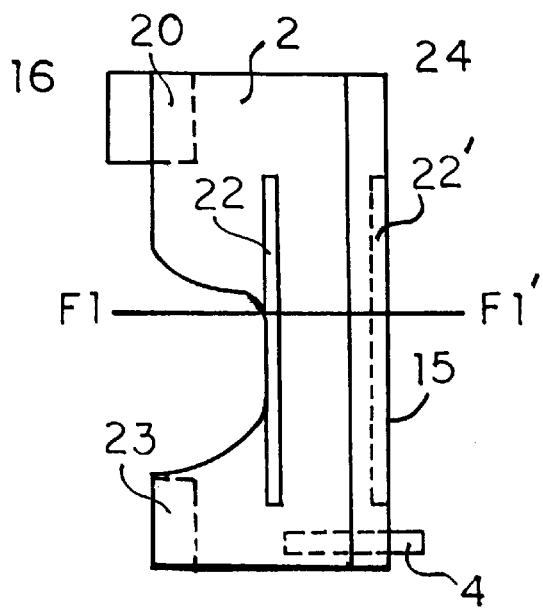
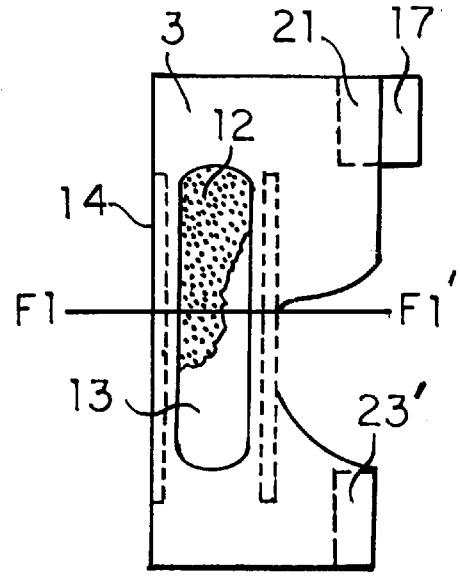

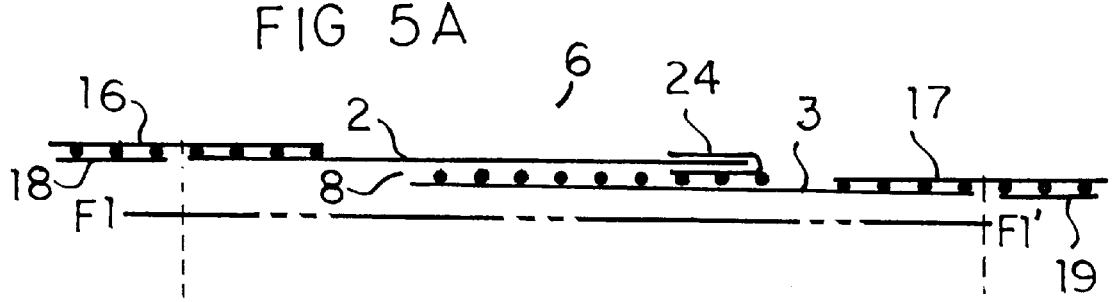
FIG 5A
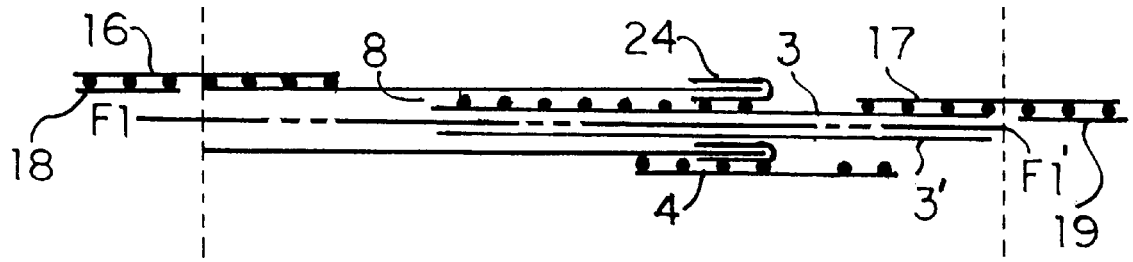
FIG 5B
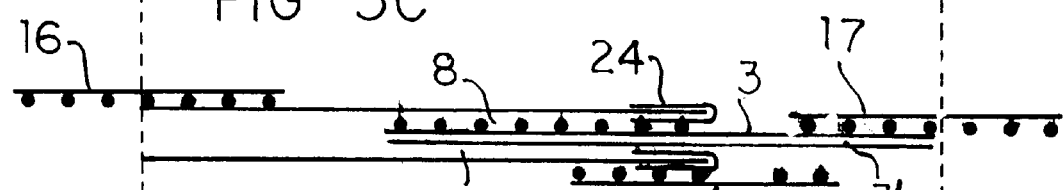
FIG 5C
FIG 5D
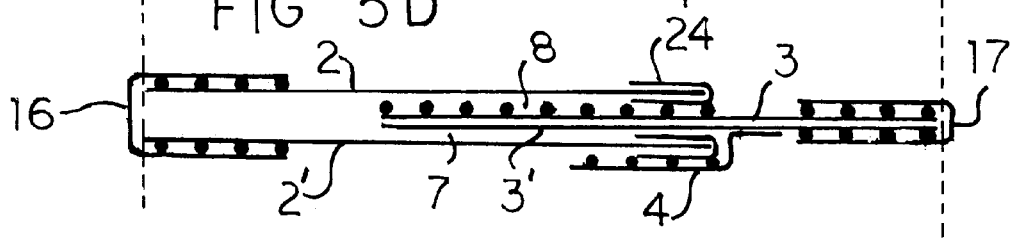
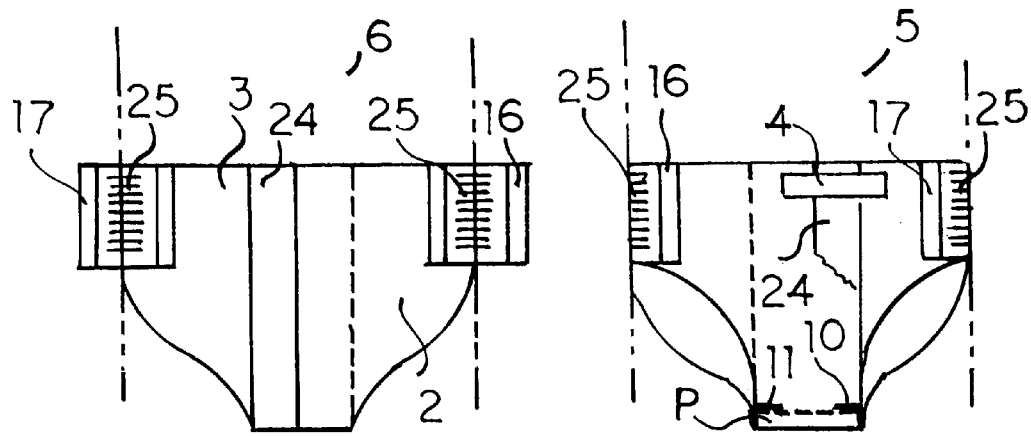
FIG 6
FIG 7

UNDERGARMENT ASSEMBLY

This application for a U.S. Patent is a continuation-in-part of U.S. application Ser. No. 08/889,461 now U.S. Pat. No. 5,864,890, for briefs which define leg and waist apertures when extensions protruding from each side of the rear panel are folded over side margins and attached to the front panel.

FIELD OF THE INVENTION

This invention relates to a garment assembly useful to infants, children and adults as an undergarment. More specifically, these garments are manufactured from continuous webs with or without an absorbent pad as an integral part thereof, or the garment can include an adhesive zone with a releasable cover strip which is removed for attachment of a pre-selected pad of the user's choice, for example, a preferred brand of hygienic pad for feminine use.

Garments of this invention are referred to as underpants or briefs for adults, or training pants for young children, and with an absorbent pad attached inside, as protective panties for feminine use or incontinent briefs for adult use. Shaped pads with pre-selected absorbency can also be used as diapers for children.

While some known incontinent products are expandable so they can be applied while the user is standing, the instant briefs are applied to the user in the same manner as disposable diapers, and after folding the front panel against the wearer, the front and rear panels are connected with tapes extending from a panel, preferably the rear panel.

BACKGROUND OF THE INVENTION

One important distinction of the '461 briefs over prior art garments is the front opening feature which is achieved by overlapping half width segments in a longitudinally extending zone and bonding the half segments together in the overlapped zone of the rear panel while leaving the overlapped zone of the front panel unbonded to thereby provide a front panel opening.

Briefs heretofore described in prior art (Class 2- garment) are normally made from textile fabrics, and being hand sewn or knitted as unitary items, are formed or assembled to have full width front and rear panels, contingous if knitted, or joined by sewn seams along side margins.

Textile garments can include front openings for male urinary functions, but with an expandable continuous elastic waistband rather than an openable panel.

The prior art in U.S. Class 128 for sanitary napkins and Class 604 for disposable diapers is replete with examples of the abovementioned improvements and features including the hourglass shape of U.S. Pat. No. 3,461,871 to Foote (1963) and 3,368,562 to Vogt (1968) and the important addition of leg elastics per U.S. Pat. No. 3,860,003 to Buell.

Thus, while substantial art exists for absorbent diaper features, there is scant teaching on incontinent pants or briefs with panels that can be opened for urinary functions, and with the front 'fly' open, be easily dropped to the user's knees for excretory functions.

U.S. Pat. No. 4,944,733 describes a diaper with a front opening for use in toilet training or for use by incontinent adults wherin the absorbent padding layer (28) is located between the inner layer (19) and outer layer (24), and is held therein by secure attachment of the inner and outer layers 19 and 24 respectively—around their entire periphery.

The instant brief as well as briefs of '461 are not constructed with an absorbent pad/agent as part of the garment, but as briefs that can accept inserts like absorbent pads or feminine hygienic pads.

U.S. Pat. No. 4,615,695 to Cooper describes a combination diaper training pant with the typical hourglass shape, but it also includes absorbent material between the inner pervious sheet and the outer impervious material, again being limited to a product with an integral absorbent pad. Patent '695 shows a front opening in both the impervious panel and the inner pervious absorbent padding.

In the instant invention and the briefs of '461, a front opening is constructed by longitudinally overlapping half width webs with the advantage that one or both of the marginal edges can be enclosed with folded strips that define a 'reinforced' front 'fly' without further processing of materials except along longitudinal lines until the product is assembled and ready for separation into discreet units, thus being well adapted for high speed fabrication.

SUMMARY OF THE INVENTION

The briefs of '461 are a complete assembly and require that a user 'steps into' the garment normally while standing.

The instant invention does not have apertures since it would be presented to the user in flat unfolded form, and like a disposable diaper, requires folding about a transverse line or the wearers body, after which the side tapes extending from both side margins are folded and attached to the other panel.

The briefs of '461 normally require the standing user to 'step into' the briefs, whereas the instant briefs can be applied while the user is in a prone position (like a disposable diaper) while retaining the front opening feature desireable for training children to open the front panel while performing urinary or excremental functions.

Side tapes for connecting front to rear panels can be made for releasable attachment to facilitate partial removal of the briefs if desired.

The same unfolded configuration and utility applies to substantially bedridden patients that can still get up for bodily waste function but who are not able to 'step into' the brief when applied.

In another embodiment, a selected portion of the inside surface of the briefs can be adhesively coated and covered with a removable release strip to accept absorbent pads optimally shaped and sized for the amounts of fluids/waste being discharged.

The completed briefs of '461 can accept absorbent pad inserts, but it is noted that to adhere the pad to the brief before wear requires that the user must separate the waist aperture for clearance.

With the instant briefs, a pad can be easily attached while the briefs remain flat and unfolded.

The inventive briefs can also have 'securement' flaps extending from the midpoint of the open flat length orientation, and the flaps can be folded over and attached to cover edges of the pad insert to minimize chafing.

In the '461 completed briefs, securement flaps would extend into each leg aperture and it would be difficult to remove the adhesive cover strip while being worn, or if the strip is removed beforehand, could stick to the inside of the wearer's legs when applied.

The securement flaps could be part of '461 briefs, but if adhesive cover strips are removed before use, the same problem of separating the waist aperture would occur.

Another object of the invention is to have side seams extend the full length of the linear portions of side margins.

In the preferred embodiment of '461, the side margin flaps have adhesive applied to bondably attach to the front panel after the transverse fold is made For this reason, the side flaps of '461 are spaced from the waist cut line (top of brief) to avoid buildup of adhesive in the (severing) die rolls.

In the instant briefs, side margin fastening means are tapes covered with release strip haviing top edges substantially coincident with the top edges of the garment waist, thereby providing a non-interrupted peripheral waist aperture.

BRIEF DESCRIPTION OF THE DRAWINGS

FIG. 1 is a perspective rear plan view of the inside of the instant briefs illustrating securement extensions of one segment of the assembly.

FIG. 2 is a plan front view of the brief illustrating the left and right side half width segments overlapped and assembled.

FIG. 3 Is a front plan view of the left half width segment illustrating a central adhesive receptor area for attachment of the upper half of the right side segment.

FIG. 4 is a front plan view illustrating a central adhesive area on the inside of the crotch area as shown in perspective of FIG. 1

FIG. 5A is an end view looking downwars along sight line 5—5. In FIGS. 2 and 5, the fold line is in front of the segment (closest to viewer).

FIG. 5B is a top view along sight line 5—5 after the instant brief has been applied and folded by the user and before the user connects the front and rear panels with side tapes.

FIG. 5C is a view like FIG. 5B with the fold line removed for clarity anf with tape release strips removed to prepare for side margin connections by the user.

FIG. 5D is an end view of the instant brief along sight line 5—5 after the brief is in place illustrating how the user attaches side tape connections to complete the briefs while applied on the body.

FIG. 6 is a rear plan view of briefs illustrating the tapes protruding from each side margin.

FIG. 7 is a front plan view of the brief illustrating the side tapes attached to the side margins of the front panel and the front panel closure tape as attached by the wearer.

DETAILED DESCRIPTION

In FIG. 1, the undegarment assembly referred to hereinafter as briefs 1 is comprised of first and second half panels each having a length between the top margin 5' of panel 5 and bottom margin 6' of panel 6 and each having a width substantially equal to one half of the garment width plus the amount of overlap between first segment 2 and second segment 3.

In the manufacturing process, segment 2 (still in web form before being cut into a discreet shape) is advanced along a path, and the other segment 3 (still in web form) is superposed on top (see also FIG. 2) and advanced along the same path.

In FIG. 2, the brief assembly includes half width segments 2 and 3 each having a leg cutout along one edge, with segments superposed in partial overlapping relationship to form a two piece assembly comprising front panel 5 and rear panel 6.

In FIGS. 1 and 2, the inside facing surfaces between segments 2 and 3 are bonded together in overlapped central area 8 from top margin 6' to the transverse fold line F1–F1' forming a unitary rear panel 6.

In FIG. 2, inside mating surfaces between segments 2 and 3 in central overlapped area 9 are left unbonded between F1–F1' and margin 5' to provide a panel opening 7, 7'(shown at the bottom of FIG. 1) in front panel 5.

In FIG. 2, bottom portions of unattached segments 2, 3 are held together by the extended free end of tape 4 protruding from margin 15 of segment 2 (see FIG. 3). When held together with tape 4, segments 2 and 3 form front panel 5 (see FIG. 2) and the inside mating surface of panel 3 are left unbonded to provide a front panel opening (see 7, 7' of FIG. 1)

In the illustrations of FIGS. 1 and 2, the front segment 3 is cut away to expose adhesive bonding 8 between the superposed segments 2, 3 in the overlapped central zone 9 (see FIG. 2) to form the unitary rear panel 6.

In FIG. 1, centrally located securement flap 10 extends from segment 2 and securement flap 11 extends from segment 3.

In FIG. 1, the inside surfaces 10', 11' of securement flaps 10,11 can be selectively coated with adhesive (not shown) or can have an impervious coating to prevent leakage from an absorbent pad P (see FIG. 7) bonded to adhesively coated receptor area 12.

In another embodiment of FIG. 1, the extension flaps are created by a separate piece adhered to the inside surface of segment 2 and extending beyond central margins 14 of segment 3 (see FIG. 4) and 15 of segment 2 (see FIG. 3).

In FIGS. 2 to 6, securement flaps 10 and 11 are not shown for clarity, but in FIG. 7 are shown in phantom attached to a pad P (also in phantom).

FIGS. 1 to 7 illustrate the fastening means 16,17 used to secure the front and rear panels.

In FIG. 2 panel fastening means 16, 17 extend from segment 2 and 3 respectively. In FIG. 1, tape 16 is covered by release strip 18 and tape 17 is covered by release strip 19.

In FIG. 3, tape 16 can have cover strip 18, or be temporarily attached to a release coated inside surface area 20 (shown phantom) and likewise in FIG. 4, tape 17 can be attached to release coated inside surface area 21.

In FIG. 3, elastic strands (not shown) are ahesively attached to receptor area 22, 22' under very low tension to provide only minimal contraction and shirring of the briefs, thus providing a flatter central zone for attaching a preselected pad (P of FIG. 7) after removing cover strip 13 shown in FIGS. 1 and 4

The separate absorbent pad (insert) would be adhered to receptor area 12 on the inside of the brief before it is folded around the user's torso and attached along side margins.

After the brief assembly 1 is being placed and folded around the torso to create closed leg and waist apertures, fastening means 16 and 17 are folded around the linear side margins of the superposed front segments and attached to receptor areas 23, 23'.

In FIG. 3, the linear margin 15 is covered with a v-folded reinforcing strip 24 (not shown in FIG. 4 for clarity).

In FIGS. 5A through 5D, only segment 2 has the v-folded strip, noting that after being folded over the torso of the wearer (see FIG. 5B) segments that form the tape connected front panel are illustrated below fold line F1–F1'(is not shown in FIGS. 5C and 5D for clarity).

FIG. 5A is viewed downwardly, specifically noting that the segments 2 and 3 are the overlapped segments for both the rear panel (top margin nearest viewer) and the front panel (farthest from viewer).

The instant assembly of the invention is shown in FIG. 5A.

FIGS. 5B through 5D illustrate the sequence of user manipulations including attachment of a pad P before use, securing the pad by use of flaps 10 and 11, and then applying the assembly, folding it around the user's crotch, and connecting side tapes to secure the leg and waist apertures like disposable diapers.

FIG. 6 illustrates tapes 16, 17 extending from rear panel 6 and having central elastic portions 25.

The front view of FIG. 7 illustrates the brief assembly after the above assembly functions have been performed by the user noting that pad P can be secured by flaps 10, 11 or, with impervious coating of the flaps, can be attached to adhesive on the sides and top of the absorbent pad P.

It is furthermore to be understood that the present invention may be embodied in other specific forms without departing from the spirit or special attributes; and it is, therefore, desired that the present embodiments be considered in all respects as illustrative, and therefore, not restrictive, reference being made to the appended claims rather than to the foregoing description to indicate the scope of the invention.

I claim:

1. A garment having an upper rear panel portion and a lower front panel portion comprising:

first and second shaped segments each having a length between top and bottom margins of said garment and a width substantially equal to one half width of said garment, said first and second shaped segments superposed in a partially overlapped mirror-image orientation forming overlapped first and second segments and innermost and outermost segments, said mirror image orientation defining a longitudinally extending overlapped central area of said garment, said shaped segments including curvilinear cutouts from each segment along longitudinal side margins most remote from said overlapped areas, said rear panel including said first and second segments bonded together in a preselected portion of said overlapped central area, said front panel opening defined by non-bonded facing surfaces of said superposed segments in said longitudinally overlapped central area, fastening means protruding from each non-overlapped side margin of said rear panel, and, at least one central fastening means attached to said first segment of said front panel for securement of said first and second segments at a top of said front panel opening.

2. The garment of claim 1 wherein said protruding side fastening means have a length substantially equal to the linear side margins of a connected brief.

3. The garment of claim 1 wherein said fastening means have at least one end with protruberances that attach to a receptor area.

4. The garment of claim 1 wherein at least a portion of said fastening means is elastic.

5. The garment of claim 1 wherein said fastening means is attached to a release coated receptor area on the surface of a segment.

6. The garment of claim 1 wherein said fastening means are tapes having the extended free end covered with a releasable strip.

7. The garment of claim 1 wherein the overlapped segments include spaced longitudinal portions with margins, and elastic members are bondably secured along the spaced longitudinal portions adjacent to the margins of said overlapped segments.

8. The garment of claim 1 wherein said protruding side extensions are tapes folded and attached to the inside surface of said rear panel and said inside surface is release coated.

9. The garment of claim 1 wherein said side margin fastening means are tapes having adhesive coating on one extended surface that is attached over a release coated outside surface of the rear panel.

10. The garment of claim 1 wherein said preselected bonded portion between overlaped segments extends between lower portions of the overlappped segments of said front panel.

11. The garment of claim 1 wherein said central fastening means is attached to one segment and has at least one end with protruberances that attach to a receptor area of a different segment.

12. The garment of claim 1 wherein at least a portion of said central fastening means is elastic.

13. The garment of claim 1 wherein the central fastening means is attached to a receptor area having release coating.

14. The garment of claim 1 including a release coated strip and an underlying adhesive area for attachment of an absorbent pad to an inner surface of said overlapped area.

15. The garment of claim 1 wherein the cutouts in side margins of said first and second segments include securement flaps extending from said overlapped central area, said securement flaps located substantially midway between said top and bottom margins of said garment.

16. The garment of claim 15 wherein the inside surface of said securement flaps is adhesively coated and covered with release strips.

17. The garment of claim 15 wherein said securement flaps are at opposite side margins of a separate substantially rectangular segment superposed on and attached to a central longitudinal overlapped area.

18. The garment of claim 15 wherein said securement flaps have an impervious coating on at least a portion therof.

19. The garment of claim 1 wherein said innermost segment has an impervious coating on the inside surface therof.

* * * * *